United States Patent
Ohno et al.

(10) Patent No.: US 8,404,906 B2
(45) Date of Patent: Mar. 26, 2013

(54) PROCESS FOR PRODUCING 1,2,3,4-TETRACHLOROHEXAFLUOROBUTANE

(75) Inventors: Hiromoto Ohno, Minato-ku (JP); Toshio Ohi, Minato-ku (JP); Takami Ohe, Minato-ku (JP)

(73) Assignee: Showa Denko K.K., Tokyo (JP)

( * ) Notice: Subject to any disclaimer, the term of this patent is extended or adjusted under 35 U.S.C. 154(b) by 154 days.

(21) Appl. No.: 13/002,223

(22) PCT Filed: Jun. 24, 2009

(86) PCT No.: PCT/JP2009/061453
§ 371 (c)(1),
(2), (4) Date: Dec. 30, 2010

(87) PCT Pub. No.: WO2010/001774
PCT Pub. Date: Jan. 7, 2010

(65) Prior Publication Data
US 2011/0112341 A1      May 12, 2011

(30) Foreign Application Priority Data

Jul. 1, 2008   (JP) ................................. 2008-172540

(51) Int. Cl.
C07C 17/00       (2006.01)
C07C 17/38       (2006.01)

(52) U.S. Cl. .......................... 570/161; 570/177; 570/178

(58) Field of Classification Search .................. 570/161, 570/177, 178
See application file for complete search history.

(56) References Cited

U.S. PATENT DOCUMENTS 7,799,959 B2     9/2010   Ohno et al.

FOREIGN PATENT DOCUMENTS

JP     2006-342059 A    12/2006
WO    2007/125975 A1   11/2007

OTHER PUBLICATIONS

Encyclopedia Chemistry, Kyoritsu Shuppan Co., Ltd., 17 edition, Mar. 10, 1975, p. 786.

*Primary Examiner* — Jafar Parsa
(74) *Attorney, Agent, or Firm* — Sughrue Mion, PLLC

(57) ABSTRACT

The present invention provides a process for producing 1,2,3,4-tetrachlorohexafluorobutane having a high purity at a low cost industrially and efficiently. The process for producing 1,2,3,4-tetrachlorohexafluorobutane according to the present invention comprises a step of allowing 1,2,3,4-tetrachlorobutane to react with a fluorine gas to prepare a reaction product containing 1,2,3,4-tetrachlorohexafluorobutane and hydrogen-containing compounds as an impurity, and a step of introducing the reaction product into single or plural distillation columns and distilling to separate the hydrogen-containing compounds from the reaction product and thereby preparing purified 1,2,3,4-tetrachlorohexafluorobutane wherein the at least one of distillation columns has a theoretical plate number of 15 or more.

8 Claims, No Drawings

PROCESS FOR PRODUCING 1,2,3,4-TETRACHLOROHEXAFLUOROBUTANE

TECHNICAL FILED

The present invention relates to a process for producing 1,2,3,4-tetrachlorohexafluorobutane. More specifically, it relates to a process for efficiently producing high purity 1,2,3,4-tetrachlorohexafluorobutane, which is useful as a raw material for synthesizing hexafluoro-1,3-butadiene that is notable as semiconductor etching gases and the like.

BACKGROUND ART 1,2,3,4-tetrachlorohexafluorobutane is an important compound as a raw material for synthesizing hexafluoro-1,3-butadiene that is notable as an etching gas used in fine processing for semiconductors.

As a process for producing 1,2,3,4-tetrachlorohexafluorobutane, there is, for example, a known process such that a compound represented by the formula $CClX^1X^2—CClX^3—CClX^4—CClX^5X^6$ ($X^1$ to $X^6$ are each independently a hydrogen atom or a fluorine atom) is allowed to react with fluorine in a liquid phase (referred to Patent document 1).

Patent document 1 discloses, as a solvent, perfluoroalkanes, perfluoroethers, perfluoropolyethers, chlorinated hydrocarbons and perfluoroalkylamines, and also discloses that it is especially preferred to use 1,2,3,4-tetrachlorohexafluorobutane as a solvent for fluorination reaction because there is no need of separation between the solvent and a reaction product. Patent document 1, however, still has an objective in the point of producing an aimed product in a high purity industrially, economically and efficiently because a reaction raw material is diluted with the solvent to carry out the fluorination reaction at low concentration.

PRIOR ART

Patent Document

Patent Document 1: JP-A-2006-342059

SUMMARY OF THE INVENTION

Subject to be Solved by the Invention

It is an object of the present invention to provide a process for producing 1,2,3,4-tetrachlorohexafluorobutane in a high purity industrially and efficiently at a low cost.

Means for Solving the Subject

The present inventors have been earnestly studied to solve the above subject. They found that when 1,2,3,4-tetrachlorobutane is allowed to react with a fluorine gas in the absence of a catalyst to produce 1,2,3,4-tetrachlorohexafluorobutane, the aimed 1,2,3,4-tetrachlorohexafluorobutane ($C_4Cl_4F_6$) forms pseudo azeotrope-like mixtures together with hydrogen-containing compounds which are impurities, particularly 1,2,3,4-tetrachlorotetrafluorobutane ($C_4H_2Cl_4F_4$) and 1,2,3,4-tetrachloropentafluorobutane ($C_4HCl_4F_5$) which are intermediates, and thereby it is very difficult to separate and purify the aimed 1,2,3,4-tetrachlorohexafluorobutane.

When the pseudo azeotrope-like mixtures are thus formed, for example, in the case of producing hexafluoro-1,3-butadiene using the pseudo azeotrope-like mixtures as a raw material by dechlorination reaction, the above hydrogen-containing compounds produce a byproduct such as tetrafluorobutadiene, pentafluorobutadiene, etc by the dechlorination reaction. It is very difficult to separate these compounds from hexafluoro-1,3-butadiene.

Under the circumstances, the present inventors have been further studied from the standpoint that the hydrogen-containing compounds are not contained in 1,2,3,4-tetrachlorohexafluorobutadiene to the utmost. As a result, they found that the above subject can be solved by distilling a reaction product of 1,2,3,4-tetrachlorobutane and a fluorine gas in specific conditions.

That is to say, the present invention relates to the following characteristics [1] to [9].

[1] A process for producing 1,2,3,4-tetrachlorohexafluorobutane comprising:

a step (1) of allowing 1,2,3,4-tetrachlorobutane to react with a fluorine gas to produce a reaction product comprising 1,2,3,4-tetrachlorohexafluorobutane and hydrogen-containing compounds as an impurity, and a step (2) of introducing the reaction product into single or plural distillation columns and distilling to separate the hydrogen-containing compounds from the reaction product and thereby preparing purified 1,2,3,4-tetrachlorohexafluorobutane, wherein at least one of the distillation columns has a theoretical plate number of 15 or more.

[2] The process for producing 1,2,3,4-tetrachlorohexafluorobutane according to [1] wherein at least one of the distillation columns has a theoretical plate number of 25 or more.

[3] The process for producing 1,2,3,4-tetrachlorohexafluorobutane according to [1] wherein the distillation columns comprises a first distillation column having a theoretical plate number of 15 or more and a second distillation column having a theoretical plate number of 25 or more, and the step (2) comprises a step (2a) of introducing the reaction product into the first distillation column and distilling and thereby separating the hydrogen-containing compounds from the reaction product to prepare a distillate mainly containing 1,2,3,4-tetrachlorohexafluorobutane from the top of the first distillation column, and a step (2b) of introducing the distillate into the second distillation column and distilling to prepare purified 1,2,3,4-tetrachlorohexafluorobutane from the bottom of the second distillation column.

[4] The process for producing 1,2,3,4-tetrachlorohexafluorobutane according to [1] wherein at least one of the hydrogen-containing compounds is 1,2,3,4-tetrachlorotrifluorobutane, 1,2,3,4-tetrachlorotetrafluorobutane or 1,2,3,4-tetrachloropentafluorobutane.

[5] The process for producing 1,2,3,4-tetrachlorohexafluorobutane according to [1] wherein the reaction product prepared in the step (1) has a concentration of 1,2,3,4-tetrachlorohexafluorobutane of not less than 80% by mass.

[6] The process for producing 1,2,3,4-tetrachlorohexafluorobutane according to [1] wherein the reaction product prepared in the step (1) has a concentration of the hydrogen-containing compounds of not more than 7.0% by mass.

[7] The process for producing 1,2,3,4-tetrachlorohexafluorobutane according to [1] wherein the 1,2,3,4-tetrachlorohexafluorobutane purified in the step (2) has a purity of not less than 99.0% by mass.

[8] The process for producing 1,2,3,4-tetrachlorohexafluorobutane according to [2] wherein the 1,2,3,4-tetrachlorohexafluorobutane purified in the step (2) has a purity of not less than 99.95% by mass.

[9] The process for producing 1,2,3,4-tetrachlorohexafluorobutane according to [3] wherein the 1,2,3,4-tetrachlorohexafluorobutane purified in the step (2b) has a purity of not less than 99.99% by mass.

Effect of the Invention

According to the present invention, high purity 1,2,3,4-tetrachlorohexafluorobutane can be produced industrially and efficiently at a low cost from 1,2,3,4-tetrachlorobutane.

EMBODIMENT FOR CARRYING OUT THE INVENTION

The process for producing 1,2,3,4-tetrachlorohexafluorobutane according to the present invention will be described in detail below.

The process for producing 1,2,3,4-tetrachlorohexafluorobutane according to the present invention comprises:

a step (1) of allowing 1,2,3,4-tetrachlorobutane to react with a fluorine gas to produce a reaction product comprising 1,2,3,4-tetrachlorohexafluorobutane and hydrogen-containing compounds which are impurities, and a step (2) of introducing the reaction product into single or plural distillation columns and distilling to separate the hydrogen-containing compounds from the reaction product and thereby preparing purified 1, 2, 3, 4-tetrachlorohexafluorobutane, wherein at least one of the distillation columns has a theoretical plate number of 15 or more.

[Step (1)]

In the step (1), 1,2,3,4-tetrachlorobutane used as a starting material is prepared as a byproduct in the step of, for example, the industrial production of a chloroprene rubber.

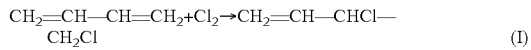

$$CH_2=CH—CH=CH_2+Cl_2 \rightarrow CH_2=CH—CHCl—CH_2Cl \quad (I)$$

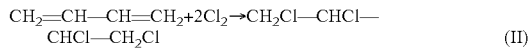

$$CH_2=CH—CH=CH_2+2Cl_2 \rightarrow CH_2Cl—CHCl—CHCl—CH_2Cl \quad (II)$$

The formula (I) shows a main reaction in the production of a chloroprene rubber, and the formula (II) shows an example of a side reaction, which is proceeded simultaneously in the progress of the reaction represented by the formula (I). In conventionally producing a chloroprene rubber, 1,2,3,4-tetrachlorobutane formed by the side reaction represented by the formula (II) is made into harmless one by incineration treatment and the like together with other byproducts (chlorides) and put into the discard.

In the present invention, for example, the 1,2,3,4-tetrachlorobutane, which is formed as a byproduct in the production step of the chloroprene rubber and conventionally has been discarded, is separated and recovered and then can be used again as a starting material.

As shown in the reaction formula (III), 3,4-dichlorobutene-1, which is an intermediate in the production step of the chloroprene rubber and a product of the formula (I), is subjected to chlorination reaction to prepare 1,2,3,4-tetrachlorobutane.

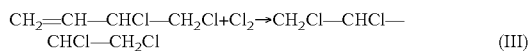

$$CH_2=CH—CHCl—CH_2Cl+Cl_2 \rightarrow CH_2Cl—CHCl—CHCl—CH_2Cl \quad (III)$$

In the case of using 1,2,3,4-tetrachlorobutane as a starting material, it has a purity of preferably not less than 95% by mass, more preferably not less than 98% by mass. Moreover, 1,2,3,4-tetrachlorobutane has optical isomers of a dl form and a meso form. The dl form has a melting point (mp) of not higher than 0° C. and a boiling point (bp) of about 213° C., and is a liquid state at room temperature, while the meso form has a melting point of about 73° C. and a boiling point of about 213° C., and is a white solid state at room temperature. Therefore, it is possible to separate the dl and meso forms utilizing the difference on their properties.

In the present invention, 1,2,3,4-tetrachlorobutane, which is a starting material, has a dl form content of preferably not less than 40% by mass. As the dl form content is higher, it is possible to dissolve it in a reaction solvent and perform the reaction at lower temperatures. Therefore, C—C cleavage and excessive fluorination hardly proceed and thereby an aimed product can be prepared in a high yield.

In the production process of the present invention, the reaction in the step (1) is preferably carried out in the presence of the solvent although it can be carried out in the absence of the solvent by controlling the conditions such as the reaction temperature or the concentration of fluorine fed to be mild. Examples of the solvent used in the present invention may include perfluorocarbons, perchlorocarbons and chlorofluorocarbons.

In the step (1), the reaction of 1,2,3,4-tetrachlorobutane and a fluorine gas can be carried out by feeding 1,2,3,4-tetrachlorobutane, which is a starting material, to the solvent and then feeding the fluorine gas to the solvent. The reaction temperature is preferably 0 to 100° C., more preferably 10 to 80° C., furthermore preferably 20 to 50° C.

When the reaction product prepared in the step (1) contains the solvent, it is preferred to separate the solvent firstly by a known method, for example, distillation. The reaction product after the solvent separation (hereinafter occasionally referred to "crude 1,2,3,4-tetrachlorohexafluorobutane") has a 1,2,3,4-tetrachlorohexafluorobutane concentration of preferably not less than 80% by mass, more preferably not less than 90% by mass. In order that the reaction product has a 1,2,3,4-tetrachlorohexafluorobutane concentration in the above range, it is important to control the reaction temperature to be low and to depress the generation of pentachloropentafluorobutane which is a byproduct.

The crude 1,2,3,4-tetrachlorohexafluorobutane contains, as impurities, hydrogen-containing compounds such as tetrachlorotetrafluorobutane ($C_4H_2Cl_4F_4$), tetrachloropentafluorobutane ($C_4HCl_4F_5$), pentachlorotetrafluorobutane ($C_4HCl_5F_4$), trichloropentafluorobutane ($C_4H_2Cl_3F_5$), trichlorohexafluorobutane ($C_4HCl_3F_6$) etc; and chlorofluorocarbons such as pentachloropentafluorobutane ($C_4Cl_5F_5$) and trichloroheptafluorobutane ($C_4Cl_3F_7$) etc.

The present inventors carry out measurement on distillation separation of the impurities and the aimed 1,2,3,4-tetrachlorohexafluorobutane and gas-liquid equilibrium and determine a relative volatility. The relative volatility is described in Encyclopedia Chemistry published by Kyoritsu Shuppan Co., Ltd. Mar. 10, 1975, 17 edition P.786 as follows. The relative volatility is a measure of the difficulty of liquid volatilization or evaporation. The volatility of a purity material is equal to the vapor pressure. The volatility of a component in a solution is represented by p/x wherein x is a molar fraction of the component and p is a partial pressure of the component in the gas phase equilibrium to the solution. When the molar fraction in the gas phase is y, the ratio y/x can be also referred to volatility. However, the y/x is usually referred to an equilibrium coefficient represented by K. The ratio of volatilities of different components or equilibrium coefficients thereof is referred to relative volatility and is usually represented by α. An ideal solution satisfies p/x=P wherein P is a vapor pressure of the component as a pure material. Therefore, the relative volatility αAB of A component to B component is equal to PA/PB.

As a result of determining the relative volatility, it is found that it is difficult to separate the impurities, particularly the hydrogen-containing compounds from the aimed 1,2,3,4-tetrachlorohexafluorobutane, and also found that since tetrachloropentafluorobutane and tetrachlorotetrafluorobutane form a pseudo azeotrope-like mixture, it is very difficult to separate and purify. Concerning to the relative volatility, tetrachloropentafluorobutane has a relative volatility α of about 1.18, tetrachlorotetrafluorobutane has an α of about 1.30 so that tetrachloropentafluorobutane is a material which is particularly difficultly separated.

Furthermore, when 1,2,3,4-tetrachlorohexafluorobutane containing the above hydrogen-containing compounds is used as a material for producing hexafluoro-1,3-butadiene which is useful as an etching gas in fine processing for semiconductors, pentafluorobutadiene, tetrafluorobutadiene and the like are produced as by-products by dechlorination reaction. These by-products are materials which are difficult to be separated from the aimed hexafluoro-1,3-butadiene. Accordingly, it is desired that 1,2,3,4-tetrachlorohexafluorobutane does not contain the hydrogen-containing compounds.

In order to efficiently separate the hydrogen-containing compounds in the following step (2), the reaction product (crude 1,2,3,4-tetrachlorohexafluorobutane) prepared in the step (1) has a hydrogen-containing compound concentration of preferably not more than 7% by mass, more preferably not more than 5% by mass. In order to be the hydrogen-containing compound concentration in the reaction product in the above range, it is important to perform the reaction with a fluorine gas completely.

[Step (2)]

In the step (2), the reaction product (crude 1,2,3,4-tetrachlorohexafluorobutane) prepared in the step (1) is introduced into a distillation column and distilled to separate the impurities containing the hydrogen-containing compounds from the reaction product and thereby purified 1,2,3,4-tetrachlorohexafluorobutane is prepared.

The theoretical plate number of the distillation column is 15 or more, preferably 25 or more, more preferably 25 to 50. One distillation column may be used or two or more distillation columns may be used. In the case of using two or more distillation columns, it is preferred that the first distillation column has a theoretical plate number of 15 or more and the second distillation column has a theoretical plate number of 25 or more. In this case, the step (2) comprises a step (2a) of introducing the reaction product prepared in the step (1) to the first distillation column and distilling to separate the hydrogen-containing compounds from the reaction product and thereby preparing a distillate mainly containing 1,2,3,4-tetrachlorohexafluorobutane from the top of the first distillation column, and a step (2b) of introducing the distillate to the second distillation column and distilling, and thereby preparing purified 1,2,3,4-tetrachlorohexafluorobutane from the bottom of the second distillation column.

The pressure of the distillation column is 1 kPa to 0.1 MPa, preferably 1 kPa to 0.05 MPa, and the temperature thereof is 50 to 150° C., preferably 90 to 145° C. Moreover, the reflux ratio is preferably 15 to 20. In the case of using two or more distillation columns, the procedure conditions of the distillation columns may be the same or different each other.

The reaction product (crude 1,2,3,4-tetrachlorohexafluorobutane) prepared in the step (1) is distilled using the distillation column having the above theoretical plate number or more, and thereby impurities containing the hydrogen-containing compounds are separated from the reaction product to prepare purified 1,2,3,4-tetrachlorohexafluorobutane having a high purity. The purified 1,2,3,4-tetrachlorohexafluorobutane has a purity of not less than 99.0% by mass, more preferably not less than 99.95% by mass, furthermore preferably not less than 99.99% by mass. The concentration of the hydrogen-containing compounds, which are impurities, is preferably not more than 1.0% by mass, more preferably not more than 0.05% by mass, furthermore preferably not more than 0.01% by mass. The hydrogen-containing compounds separated as impurities, such as 1,2,3,4-tetrachloropentafluorobutane or 1,2,3,4-tetrachlorotetrafluorobutane may be re-used by circulating to the reactor of the step (1) again.

The high purity 1,2,3,4-tetrachlorohexafluorobutane thus prepared is subjected to dechlorination reaction to prepare high purity hexafluoro-1,3-butadiene. The dechlorination reaction can be carried out by a known method.

EXAMPLE

The present invention will be described in more detail with reference to the following examples below but it should be construed that the invention is in no way limited to those examples.

Production Example 1,3-butadiene industrially produced was subjected to chlorination reaction to prepare 3,4-dichlorobutene-1. The 3,4-dichlorobutene-1 was subjected to chlorination reaction by a chlorine gas in the absence of a solvent and a resultant mixture was subjected to separation purification by distillation to prepare 1,2,3,4-tetrachlorobutane. As a result of analysis by a gas chromatography, this 1,2,3,4-tetrachlorobutane had a purity of 99.5% by mass and a proportion of dl form to meso form of about 49/51.

Example 1

Step (1)

To a 10 L internal volume SUS304 (Teflon (Trade Mark) Lining) reactor, 3800 g of tetrachloromethane was put as a solvent, and 200 g of hydrogen fluoride was dissolved in the solvent and 1000 g of 1,2,3,4-tetrachlorobutane prepared in the production example was introduced. A nitrogen gas was introduced at a pressure of 1.0 MPa to carry out leak test. Thereafter, the reactor was purged with nitrogen, and the temperature was kept at 35° C. while stirring the mixture. Next, the reaction was started while continuously feeding 50% by volume fluorine gas diluted with a nitrogen gas at a pressure of 0.2 MPa at a rate of 1000 ml/min to a liquid phase part from a gas introducing tube attached in the reactor. About 32 hr after from the reaction start, when the fluorine concentration in exhaust gas in the reactor was about 49% and fluorine gas was not almost used, the fluorine gas feeding was stopped and the reaction was finished. The solvent was distilled off and then the resulting crude 1,2,3,4-tetrachlorohexafluorobutane was analyzed by a gas chromatography. The analysis results are shown in Table 1.

TABLE 1

| Component | % by mass |
| --- | --- |
| 1,2,3,4-tetrachlorohexafluorobutane | 84.0101 |
| 1,2,3,4-tetrachlorobutane | 0.0089 |
| 1,2,3,4-tetrachloropentafluorobutane | 4.8658 |
| 1,2,3,4-tetrachlorotetrafluorobutane | 1.0856 |
| Pentachlorotetrafluorobutane | 0.1028 |
| Trichloropentafluorobutane | 0.0880 |

TABLE 1-continued

| Component | % by mass |
|---|---|
| Other hydrogen-containing compounds | 0.0524 |
| Trichloroheptafluorobutane | 0.2897 |
| Pentachloropentafluorobutane | 9.2865 |
| Other compounds | 0.2102 |

Step (2)

The crude 1,2,3,4-tetrachlorohexafluorobutane prepared in the step (1) was subjected to distillation procedure in the following conditions and procedures. 1,2,3,4-tetrachlorohexafluorobutane obtained from the top of the column was analyzed by a gas chromatography. The results are shown in Table 2.

(Distillation Conditions and Procedures)
Distillation scale: Amount of Crude 1,2,3,4-tetrachlorohexafluorobutane fed; 400 g
Distillation column: Precision distillation device (manufactured by Kiriyama Glass Works Co.) Packed column 16 mm$\phi$×500 mm
Packings: HELI PACK No. 2 (TO-TOKU Engineering Corporation); about 100 ml
Theoretical plate number: 15 plates
Procedure conditions: Pressure 4 kPa; Oil bath temperature from 102 to 142° C.; Reflux ratio 20

TABLE 2

| Component | % by mass |
|---|---|
| 1,2,3,4-tetrachlorohexafluorobutane | 99.3985 |
| 1,2,3,4-tetrachlorobutane | ND |
| 1,2,3,4-tetrachloropentafluorobutane | 0.5872 |
| 1,2,3,4-tetrachlorotetrafluorobutane | 0.0138 |
| Pentachlorotetrafluorobutane | ND |
| Trichloropentafluorobutane | ND |
| Other hydrogen-containing compounds | 0.0003 |
| Trichloroheptafluorobutane | ND |
| Pentachloropentafluorobutane | ND |
| Other compounds | 0.0002 |

Example 2

The crude 1,2,3,4-tetrachlorohexafluorobutane prepared in the step (1) of Example 1 was subjected to distillation procedure in the following conditions and procedures. 1,2,3,4-tetrachlorohexafluorobutane obtained from the top of the column was analyzed by a gas chromatography. The results are shown in Table 3.

(Distillation Conditions and Procedures)
Distillation scale: Amount of Crude 1,2,3,4-tetrachlorohexafluorobutane fed; 400 g
Distillation column: Precision distillation device (manufactured by Kiriyama Glass Works Co.) Packed column 16 mm$\phi$×835 mm
Packings: HELI PACK No. 2 (TO-TOKU Engineering Corporation) about 167 ml
Theoretical plate number: 25 plates
Procedure conditions: Pressure 4 kPa; Oil bath temperature from 102 to 142° C.; Reflux ratio 20

TABLE 3

| Component | % by mass |
|---|---|
| 1,2,3,4-tetrachlorohexafluorobutane | 99.9717 |
| 1,2,3,4-tetrachloropentafluorobutane | 0.0282 |
| 1,2,3,4-tetrachlorotetrafluorobutane | 0.0001 |
| Other hydrogen-containing compounds | ND |
| Other compounds | ND |

Example 3

400 g of the crude 1,2,3,4-tetrachlorohexafluorobutane prepared in the step (1) of Example 1 was distilled, off using a distillation column having 15 theoretical plates used in Example 1 as a first distillation column and further, the resulting gas containing 1,2,3,4-tetrachlorohexafluorobutane prepared from the top of the first distillation column was introduced into a second distillation column which is a distillation column having 25 theoretical plates used in Example 2 and distilled off in the same distillation conditions (total theoretical plate number: 40 plates). A resulting distillate containing 1,2,3,4-tetrachlorohexafluorobutane prepared from the bottom of the second distillation column was analyzed by a gas chromatography. The results are shown in Table 4.

TABLE 4

| Component | % by mass |
|---|---|
| 1,2,3,4-tetrachlorohexafluorobutane | 99.9959 |
| 1,2,3,4-tetrachloropentafluorobutane | 0.0041 |
| 1,2,3,4-tetrachlorotetrafluorobutane | ND |

Comparative Example 1

The crude 1,2,3,4-tetrachlorohexafluorobutane prepared in the step (1) of Example 1 was subjected to distillation procedure in the following conditions and procedures. 1,2,3,4-tetrachlorohexafluorobutane prepared from the top of the column was analyzed by a gas chromatography. The results are shown in Table 5.

(Distillation Conditions and Procedures)
Distillation scale: Amount of Crude 1,2,3,4-tetrachlorohexafluorobutane fed; 400 g
Distillation column: Precision distillation device (manufactured by Kiriyama Glass Works Co.) Packed column 16 mm$\phi$×500 mm
Packings: HELI PACK No. 2 (TO-TOKU Engineering Corporation); about 66 ml
Theoretical plate number: 10 plates
Procedure conditions: Pressure 4 kPa; Oil bath temperature from 102 to 142° C.; Reflux ratio 20

TABLE 5

| Component | % by mass |
|---|---|
| 1,2,3,4-tetrachlorohexafluorobutane | 95.9947 |
| 1,2,3,4-tetrachlorobutane | 0.0015 |
| 1,2,3,4-tetrachloropentafluorobutane | 1.6544 |
| 1,2,3,4-tetrachlorotetrafluorobutane | 0.3583 |
| Pentachlorotetrafluorobutane | 0.0064 |
| Trichloropentafluorobutane | 0.0018 |
| Other hydrogen-containing compounds | 0.0099 |
| Trichloroheptafluorobutane | 0.0678 |

TABLE 5-continued

| Component | % by mass |
|---|---|
| Pentachloropentafluorobutane | 1.8936 |
| Other compounds | 0.0116 |

As is clear from the examples and comparative example, using the column having a theoretical plate number of 15 or more, 1,2,3,4-tetrachlorohexafluorobutane having a high purity of not less than 99% by mass, which is an aimed product, could be prepared, while using the column having a theoretical plate number of less than 15, 1,2,3,4-tetrachlorohexafluorobutane having a high purity could not be prepared.

The invention claimed is:

1. A process for producing 1,2,3,4-tetrachlorohexafluorobutane comprising:
a step (1) of allowing 1,2,3,4-tetrachlorobutane to react with a fluorine gas to produce a reaction product comprising 1,2,3,4-tetrachlorohexafluorobutane and hydrogen-containing compounds as an impurity, and
a step (2) of introducing the reaction product into single or plural distillation columns and distilling to separate the hydrogen containing compounds from the reaction product and thereby preparing purified 1,2,3,4-tetrachlorohexafluorobutane,
wherein the distillation columns comprise a first distillation column having a theoretical plate number of 15 or more and a second distillation column having a theoretical plate number of 25 or more, and
the step (2) comprises a step (2a) of introducing the reaction product into the first distillation column and distilling and thereby separating the hydrogen-containing compounds from the reaction product to prepare a distillate mainly containing 1,2,3,4-tetrachlorohexafluorobutane from the top of the first distillation column, and a step (2b) of introducing the distillate into the second distillation column and distilling to prepare purified 1,2,3,4-tetrachlorohexafluorobutane from the bottom of the second distillation column.

2. The process for producing 1,2,3,4-tetrachlorohexafluorobutane according to claim 1 wherein at least one of the distillation columns has a theoretical plate number of 25 to 50.

3. The process for producing 1,2,3,4-tetrachlorohexafluorobutane according to claim 1 wherein at least one of the hydrogen-containing compounds is 1,2,3,4-tetrachlorotrifluorobutane, 1,2,3,4-tetrachlorotetrafluorobutane or 1,2,3,4-tetrachloropentafluorobutane.

4. The process for producing 1,2,3,4-tetrachlorohexafluorobutane according to claim 1 wherein the reaction product prepared in the step (1) has a concentration of 1,2,3,4-tetrachlorohexafluorobutane of not less than 80% by mass.

5. The process for producing 1,2,3,4-tetrachlorohexafluorobutane according to claim 1 wherein the reaction product prepared in the step (1) has a concentration of the hydrogen-containing compounds of not more than 7.0% by mass.

6. The process for producing 1,2,3,4-tetrachlorohexafluorobutane according to claim 1 wherein the 1,2,3,4-tetrachlorohexafluorobutane purified in the step (2) has a purity of not less than 99.0% by mass.

7. The process for producing 1,2,3,4-tetrachlorohexafluorobutane according to claim 2 wherein the 1,2,3,4-tetrachlorohexafluorobutane purified in the step (2) has a purity of not less than 99.95% by mass.

8. The process for producing 1,2,3,4-tetrachlorohexafluorobutane according to claim 1 wherein the 1,2,3,4-tetrachlorohexafluorobutane purified in the step (2b) has a purity of not less than 99.99% by mass.

* * * * *